United States Patent
Platteeuw (10) Patent No.: US 12,214,081 B2
(45) Date of Patent: Feb. 4, 2025

(54) TABLET DOSAGE FORMULATIONS OF OLEYL PHOSPHOCHOLINE

(71) Applicant: Oblita Therapeutics BVBA, Zoersel (BE)

(72) Inventor: Johannes Jan Platteeuw, Werkhoven (NL)

(73) Assignee: Oblita Therapeutics BVBA, Zoersel (BE)

( * ) Notice: Subject to any disclaimer, the term of this patent is extended or adjusted under 35 U.S.C. 154(b) by 626 days.

(21) Appl. No.: 17/603,024

(22) PCT Filed: Apr. 10, 2020

(86) PCT No.: PCT/EP2020/060324
§ 371 (c)(1),
(2) Date: Oct. 12, 2021

(87) PCT Pub. No.: WO2020/208230
PCT Pub. Date: Oct. 15, 2020

(65) Prior Publication Data
US 2022/0183975 A1   Jun. 16, 2022

(30) Foreign Application Priority Data
Apr. 12, 2019 (EP) .................................... 19168885

(51) Int. Cl.
| A61K 9/16 | (2006.01) |
| A61K 9/20 | (2006.01) |
| A61K 9/28 | (2006.01) |
| A61K 31/685 | (2006.01) |

(52) U.S. Cl.
CPC .......... *A61K 9/1641* (2013.01); *A61K 9/1652* (2013.01); *A61K 9/1694* (2013.01); *A61K 9/2013* (2013.01); *A61K 9/2018* (2013.01); *A61K 9/205* (2013.01); *A61K 9/2054* (2013.01); *A61K 9/2095* (2013.01); *A61K 9/2813* (2013.01); *A61K 9/2826* (2013.01); *A61K 9/288* (2013.01); *A61K 9/2893* (2013.01); *A61K 31/685* (2013.01)

(58) Field of Classification Search
None
See application file for complete search history.

(56) References Cited

U.S. PATENT DOCUMENTS

2010/0227903 A1 * 9/2010 Geers ................... A61K 9/1694
514/376

FOREIGN PATENT DOCUMENTS

| WO | WO-9937289 A1 * | 7/1999 | ........... A61K 31/685 |
| WO | WO-2012069427 A1 * | 5/2012 | ........... A61K 31/685 |

* cited by examiner

*Primary Examiner* — Susan T Tran
(74) *Attorney, Agent, or Firm* — N.V. Nederlandsch Octrooibureau (57) ABSTRACT

The present invention relates to tablet dosage formulations of oleyl phosphocholine for oral administration and the processes for their preparation. Specifically, the present invention provides a process for preparing an oleyl phosphocholine containing granulate, said process comprising a blending step, a hot melt agglomeration step and a milling step. The present invention further provides a process for preparing a tablet comprising the oleyl phosphocholine containing granulate, said process comprising the step of preparing an OlPC containing granulate according to the invention, a blending step, a compression step, and optionally a coating step. The invention further provides any intermediate and/or en product resulting from these steps and processes.

14 Claims, 1 Drawing Sheet

TABLET DOSAGE FORMULATIONS OF OLEYL PHOSPHOCHOLINE

FIELD OF THE INVENTION

The present invention relates to tablet dosage formulations of oleyl phosphocholine (C18:1-PC or OlPC) for oral administration and the methods for their preparation.

BACKGROUND OF THE INVENTION

Miltefosine (MIL), an alkylphosphocholine, is a medicament for the treatment of parasitic diseases such as leishmaniasis, chagas and malaria, and cancer in humans and animals. It is generally used for the treatment of visceral leishmaniasis (VL).

The major advantage of miltefosine for the treatment of visceral leishmaniasis is that it can be administered orally and that no cross-resistance is observed with any other first and second line antileishmaniasis therapy. However, currently available drug formulations comprising miltefosine all suffer from limitations associated with cost, toxicity or the need for parenteral administration. Patent publication WO 99/37289 describes and addresses some of the problems associated with miltefosine formulations.

An alternative for miltefosine is the alkylphosphocholine oleyl phosphocholine (C18:1-PC or OlPC) providing, amongst others, a more effective treatment of parasitic diseases such as leishmaniasis and malaria in both humans and animals. Although the use of oleyl phosphocholine for the treatment of several diseases is suggested, the currently available formulations of oleyl phosphocholine are generally solutions, suspensions or emulsions.

The development of solid dosage formulations of oleyl phosphocholine, and specifically the development of tablets, is complicated by the low melting point (56.3° C.), high hygroscopicity (absorbing 41.67 weight percent of water when exposed to 90% RH at 25° C.) and irregular particle size and shape of oleyl phosphocholine. These characteristics make it hard to obtain homogeneous, dry powders for tableting.

Due to these characteristics, several problems occur if a standard direct compression is used to prepare a tablet dosage formulation. As oleyl phosphocholine agglomerates upon storage due to its low melting point and high hygroscopicity, it has to be well sieved before compression. This requires a lot of energy and causes the sieves to get clogged, especially at the high temperatures which occur due to friction. During the compression, the oleyl phosphocholine tends to stick to the punches. Furthermore, the resulting tablets have a greasy appearance and are covered with non-homogeneous spots.

Patent publication WO 2012/069427 A1 has partially addressed these problems by preparing a solid dosage formulation of oleyl phosphocholine, more specifically a tablet dosage formulation, via a modified wet granulation process. However, the stability of the tablet dosage formulations prepared via this process as reported in WO 2012/069427 A1 was only tested for a period of twelve months at a temperature of 30° C. and a relative humidity (RH) of 65%. This is not enough since the geographic areas with high incidence of leishmaniasis are mostly tropical, particularly because earlier stability studies have shown that oleyl phosphocholine is prone to degradation by exposure to high temperatures and humidities.

Hence, there is a need in the art for tablet dosage formulations of oleyl phosphocholine which are stable under warm (30° C.) and humid conditions (75% RH) for a period of at least 24 months and can be prepared via a process which does not suffer from technical drawbacks associated with the low melting point and high hygroscopicity of oleyl phosphocholine such as agglomeration, sticking and sieve clogging.

SUMMARY OF THE INVENTION

Considering the need in the art discussed above, the present invention provides tablet dosage formulations of oleyl phosphocholine which are stable under warm and humid conditions, preferably upon storage for at least 24 months at 30° C. and 75% RH, and the processes for their preparation, which do not suffer from technical drawbacks associated with the low melting point and high hygroscopicity of oleyl phosphocholine.

In a first aspect, the invention provides a process for preparing an olelyl phosphocholine (OlPC) containing granulate, said process comprising a blending step, a melt-agglomeration step and a milling step,
  wherein the blending step comprises preparing a mixture of olelyl phosphocholine and one or more granulation excipients, preferably at least a filler, a spacer and/or an anti-oxidant;
  wherein the melt-agglomeration step comprises preparing a granulate by heating said mixture and subjecting said heated mixture to mechanical shear force;
  wherein the milling step comprises preparing a milled granulate by cooling said granulate and milling said cooled granulate;
  wherein no solvent is added during the process for granulation.

In a preferred embodiment the melt-agglomeration step comprises hot melt extrusion, (high-shear) melt granulation or fluidized bed melt granulation.

In a particularly preferred embodiment, the invention provides a process as defined above, comprising a granulation blending step, a hot melt extrusion step and a milling step,
  wherein the granulation blending step comprises preparing a granulation mixture of olelyl phosphocholine and granulation excipients, wherein said granulation excipients comprise at least a spacer, an antioxidant and a disintegrant, and optionally a binder and/or a lubricant;
  wherein the hot melt extrusion step comprises preparing an extrudate by heating said granulation mixture and extrudating said heated granulation mixture;
  wherein the milling step comprises preparing a milled extrudate by cooling said extrudate and granulating said cooled extrudate;
  wherein no solvent is added during the process for granulation.

In a second aspect, the invention provides a process for preparing a tablet dosage formulation comprising the process for preparing an OlPC containing granulate as defined herein, a compression blending step, a compression step, and optionally a coating step,
  wherein the compression blending step comprises preparing a compression mixture by mixing said milled extrudate with compression excipients,
  wherein said compression excipients comprise at least a filler and a lubricant, and optionally a binder and/or disintegrant.

In a further aspect, the invention provides OlPC containing granulates prepared via the process presented above.

In yet further aspects, the invention provides tablet dosage formulations prepared via the process presented above, their uses as a medicament, and their uses in the treatment of parasitic diseases, preferably a parasitic disease selected from the group consisting of leishmaniasis, chagas and malaria, and cancer.

The processes of preparing the OlPC containing ganulate according to the invention (i) are dry processes, as solvents may not be added during the granulation process, and (ii) typically comprise the addition of specific granulation excipients. As a result of these two aspects of the process, a tablet dosage formulation according to the invention is more stable under warm and humid conditions than tablet dosage formulations prepared via a direct compression or a wet granulation process, as found in the prior art. Specifically, a tablet dosage formulation according to the invention is stable upon storage for at least 24 months at a temperature of 30° C. and a relative humidity of 75%, meaning that the active pharmaceutical ingredient in said tablet dosage formulation does not degrade under said conditions.

Moreover, as a result of the two aspects of the process for granulation according to the invention mentioned above, neither the process of preparing the ganulate according to the invention nor the process for preparing a tablet dosage formulation according to the invention suffer from any technical drawbacks associated with the low melting point and high hygroscopicity of oleyl phosphocholine.

Without wishing to be be bound by theory, it is believed that the interaction between the the active pharmaceutical ingredient and granulation excipients, such as a filler and/or a spacer, during the melt-agglomeration step, such as the hot melt extrusion step, leads to a favorable molecular structure of the OlPC, less prone to undesirable interactions with other active pharmaceutical ingredient molecules, excipients, (ambient) moisture, etc.

Furthermore, it is believed that the use of antioxidant inhibits the oxidation of the carbon-carbon double bond in oleyl phosphocholine, which is likely to be associated with the degradation of the active pharmaceutical ingredient.

In preferred embodiments of the invention the one or more granulation excipients comprise at least a spacer an antioxidant, and a disentegrant, and optionally a binder, a filler and/or a lubricant.

DETAILED DESCRIPTION OF THE INVENTION

Definitions

Tableting is the preparation of a tablet or tablet dosage formulation from the compounds comprised therein, wherein said compounds may be active pharmaceutical ingredients (APIs) or excipients.

Active pharmaceutical ingredients have a pharmaceutical activity in the field of parasitic diseases, preferably a parasitic disease selected from the group consisting of leishmaniasis, chagas, malaria, and cancer in the context of this application.

A tablet dosage formulation comprises a tablet core, comprising the active pharmaceutical ingredient(s), and optionally a tablet coating. The preparation of a tablet core comprises at least a granulation step, a compression blending step, and a compression step in the context of this application.

An excipient is any compound comprised in a tablet dosage formulation which is not an active pharmaceutical ingredient in the context of this application. Preferably, an excipient provides said tablet dosage formulation with structural integrity or a pharmacokinetical advantage over a corresponding tablet dosage formulation wherein said excipient is not present. For this reason, excipients can be classified according to their function. A non-limitative list of types of excipients are binders, spacers, fillers, lubricants, antioxidants and disintegrants. It is clear that an excipient may belong to several types of excipients. For example, microcrystalline cellulose may be at least a binder, a filler and a disintegrant.

A binder provides tablet dosage formulation with structural integrity by holding the compounds comprised therein together.

A spacer prevents the physical and/or chemical interaction between two or more other molecules in a tablet dosage formulation.

A filler increases the volume of a tablet dosage formulation.

A lubricant increases the homogeneity of the compounds in a tablet dosage formulation and prevents said tablet dosage formulation from adhering to process equipment or packaging material.

An antioxidant prevents the chemical oxidation of other compounds comprised in a tablet dosage formulation.

A disintegrant causes a tablet dosage formulation to disintegrate and release the active pharmaceutical ingredients comprised therein in the digestive track.

A solvent refers to an aqueous or organic solvent which may be added during the preparation of a tablet dosage formulation.

The expression "granulate" is generally understood to refer to aggregates of particles, sometimes called granules (Remington's Pharmaceutical Sciences 18th ed. 1990, page 1641).

The term "agglomeration" refers to processes wherein compounds in particulate or powder form (primary particles') are processed so as to produce a product composed of larger particles, called aggomerates or granules. Agglomeration usually involves the use of a liquid capable of binding primary particles. Melt agglomeration is a process employing a binder that is typically solid at ambient temperature and wherein the agglomeration is effected at an increased temperature, above the melting point of the binder.

Granulation is the process of forming grains or granules from a mixture of compounds, preferably wherein said grains or granules are homogeneous. A granulation process may be classified as a wet or a dry granulation process, depending on whether or not solvents are added during the process. In a particularly preferred embodiment of the invention, the "process for granulation" is a dry granulation process comprising a granulation blending step, a hot melt extrusion step and a milling step. Granulation and granulation process and process for granulation are used interchangeably in the context of this application.

A granulation excipient is an excipient which has been added during the process for granulation of the preparation of a tablet dosage formulation.

Compression is the process of preparing a tablet core with essentially the same physical size as the tablet dosage formulation, by physically compressing a compression mixture. Said tablet core may be the tablet dosage formulation, or said tablet core may undergo several coating processes before a tablet dosage formulation is formed. During said coating processes, the physical size of the (partially coated) tablet core is essentially the same as the physical size as the tablet dosage formulation. Examples of said coating processes include sugar coating and colouring.

A compression excipient is an excipient which is added after the process for granulation of the invention and during the compression blending step and before the compression step of the process for preparing a tablet dosage formulation.

Wherever the term excipient is used in this application, reference is made to both granulation excipients and compression excipients, unless explicitly stated otherwise. Wherever granulation or compression are used as a noun modifier before a specific type of excipient, reference is made to a granulation or compression excipient of that type, respectively. For example, a granulation binder should be interpreted as a granulation excipient which is a binder.

The stability of a tablet dosage formulation refers to the change of the concentration of the active pharmaceutical ingredients comprised therein over time. In a preferred instance, stability of a tablet dosage formulation refers to stability of a tablet dosage formulation under humid and warm conditions.

The degradation of the active pharmaceutical ingredients (in a tablet dosage formulation) refers to the decrease of the concentration of the active pharmaceutical ingredients comprised in the tablet dosage formulation over time.

The disintegration of a tablet dosage formulation refers to the breaking of said tablet dosage formulation into separate parts when said tablet dosage formulation is brought into contact with a fluid. Preferably, said fluid is a buffered aqueous solution. More preferably, said fluid is a 0.1 N aqueous HCl solution. Disintegration of a tablet dosage formulation may be determined using the European Pharmacopoeia 2.9.1 standard disintegration test (900 ml HCl 0.1 N) or USP <701>.

The dissolution of an active pharmaceutical ingredient comprised in a tablet dosage formulation refers to the dissolving of said active pharmaceutical ingredient in a fluid, when said tablet dosage formulation is brought into contact with said fluid. Preferably, said fluid is a buffered aqueous solution. For example, dissolution of oleyl phosphocholine comprised in a tablet dosage formulation according to the invention may refer to dissolving of oleyl phosphocholine in the fluids of the gastrointestinal tract after ingestion of said tablet dosage formulation. Dissolution of an active pharmaceutical ingredient comprised in a tablet dosage formulation may be determined using the European Pharmacopoeia 2.9.3 standard dissolution test and is typically expressed as the decrease of the weight percentage of the active pharmaceutical ingredient in said tablet dosage formulation over time. The dissolution release profile is determined by measuring the dissolution over time using the European Pharmacopoeia 2.9.3 standard dissolution test.

An active pharmaceutical ingredient comprised in a tablet dosage formulation has a stable dissolution release profile if the dissolution release profile of said active pharmaceutical ingredient does not change significantly upon storage under warm and humid conditions. Preferably, the dissolution release profile of oleyl phosphocholine comprised in a tablet dosage formulation according to the invention is considered to be stable if at least 60, 65, 70, 75 or 80 weight percent of oleyl phospocholine has been dissolved after 60 minutes, preferably at least 70 weight percent of oleyl phospocholine, more preferably at least 75 weight percent of oleyl phosphocholine, most preferably at least 80 weight percent of oleyl phospocholine, as determined by the European Pharmacopoeia 2.9.3 standard dissolution test, for all tablet dosage formulations stored up to 24 months under warm and humid conditions. Preferably, said warm and humid conditions are 25° C. and 60% RH, 30° C. and 65% RH or 30° C. and 75% RH, more preferably 30° C. and 75% RH.

A particularly stable tablet dosage formulation (under warm and humid conditions) in the context of this invention is a tablet dosage formulation, wherein, if stored under warm and humid conditions, preferably for at least 24 months at a temperature of 30° C. and a relative humidity of 75%,
the concentration of each active pharmaceutical ingredient in said tablet dosage formulation does not change by more than 5 weight percent, preferably by not more than 2.5 weight percent, more preferably by not more than 1 weight percent; and
each active pharmaceutical ingredient in said tablet dosage formulation has a stable dissolution release profile.

Storage under warm and humid conditions, in the context of this application, is the storage of a tablet dosage formulation for, in the order of increasing preference, 1, 2, 3, 6, 12, 18, 24 or 36 months in a temperature range from 20° C. to 60° C. and a relative humidity range from 20% to 100%. Preferred temperature ranges are, in the order of increasing preference, from 25° C. to 60° C., from 30° C. to 60° C., from 35° C. to 60° C., and from 40° C. to 60° C. Preferred relative humidity ranges are, in the order of increasing preference, from 50% to 100%, from 60% to 100%, from 65% to 100%, from 70% to 100%, and from 75% to 100%. Preferred warm and humid storage conditions in this context are at 25° C. and 60% RH or at 30° C. and 65% RH or at 30° C. and 75% RH or at 40° C. and 75% RH for 12 or 24 months; even more preferably at 25° C. and 60% RH or at 30° C. and 65% RH or at 30° C. and 75% RH or at 40° C. and 75% RH for 24 months; even more preferably at 30° C. and 75% RH or at 40° C. and 75% RH for 24 months; even more preferably at 30° C. and 75% RH for 24 months.

The concentration of a type of excipient in a mixture is the sum of the concentrations of the granulation excipients and the compression excipients of that type. For example, the concentration of the binder in the compression mixture in a process for preparing a tablet dosage formulation according to the invention is the sum of the weight of the granulation binder and the weight of the compression binder, divided by the weight of the compression mixture.

Processes for Preparing OlPC Containing Granulate

In a first aspect, the invention provides a process for preparing an olelyl phosphocholine (OlPC) containing granulate, said process comprising a blending step, a melt-agglomeration step and a milling step,
wherein the blending step comprises preparing a mixture of olelyl phosphocholine and one or more granulation excipients, preferably at least a filler, a spacer and/or an anti-oxidant;
wherein the melt-agglomeration step comprises preparing a granulate by heating said mixture and subjecting said heated mixture to mechanical shear force;
wherein the milling step comprises preparing a milled granulate by cooling said granulate and milling said cooled granulate;
wherein no solvent is added during the process for granulation.

In a preferred embodiment the melt-agglomeration step comprises hot melt extrusion, (high-shear) melt granulation or fluidized bed hot melt granulation. In accordance with invention, hot-melt extrusion is particularly preferred.

Thus, in a preferred embodiment a process for making an OlPC containing granulate is provided, said process comprising a granulation blending step, a hot melt extrusion step and a milling step,
wherein the granulation blending step comprises preparing a granulation mixture of olelyl phosphocholine and granulation excipients, wherein said granulation excipients comprise at least a spacer, an antioxidant and a disintegrant, and optionally a binder and/or a lubricant;

wherein the hot melt extrusion step comprises preparing an extrudate by heating said granulation mixture and extrudating said heated granulation mixture;

wherein the milling step comprises preparing a milled extrudate by cooling said extrudate and granulating said cooled extrudate;

wherein no solvent is added during the process for granulation.

All steps of a process for granulation according to the invention or a process for preparing a tablet dosage formulation according to the invention may be executed using standard equipment and methodology. For example, during the hot melt extrusion step a twin screw extruder may be used with a sieve size of 1 mm, keeping the melt temperature between 40° C. and 60° C.

In preferred embodiments of the invention, the granulation excipients comprise one, two or all of a spacer, an antioxidants, and a filler. In more preferred embodiments of the invention, the granulation excipients comprise a spacer, an antioxidants, and a filler and optionally one or more further granulation excipients, such as disintegrants, binders and lubricants.

In other preferred embodiments of the invention, the granulation excipients comprise one or more excipients selected from the group consisting of spacers, antioxidants, disintegrants, fillers, binders and lubricants. In a particularly preferred embodiment of the invention, the granulation excipients comprise a spacer, an antioxidant and a disintegrant, and optionally a filler, a binder and/or a lubricant. In a most preferred embodiment of the invention, the granulation excipients comprise a spacer, an antioxidant and a disintegrant, and optionally a binder and/or a lubricant.

The spacer to be used as a granulation excipient is preferably hydrophilic polymers, more preferably selected from the group consisting of polyethylene glycol, polyethylene glycol esters, polypropylene glycol, polypropylene glycol esters, polyvinyl pyrrolidone (PVP), poly-(2-oxazoline)s (PDX) and polyacrylic acid (PAA) and hydroxypropylmethylcellulose. In one particularly preferred embodiment of the invention, the spacer is a hydrophilic polymer selected from the group consisting of polyethylene glycol 4000 (PEG 4000, macrogol 4000) and polyethylene glycol 6000 (PEG 6000, macrogol 6000), polyvinyl pyrrolidone (PVP), poly-(2-oxazoline)s (PDX) and polyacrylic acid (PAA). More preferably, the granulation spacer in a process for agglomeration is polyethylene glycol 4000 or polyethylene glycol 6000, more preferably polyethylene glycol 6000. In certain embodiments of the invention, products comprising PEG esters in combination with other components may be used as the spacer, such as the hydrophilic grades of Gelucire, e.g. Gelucire 50/13, 44/14, 48/,16, 55/18, 35/10 and 48/09, which are based on mixtures of mono, di and triglycerides with PEG esters of fatty acids.

The antioxidant to be used as granulation excipient is preferably selected from the group consisting of alpha tocopherolacetate, Vitamin E, Vitamin E TPGS, diethylhexyl syringylidene malonate, diisopropyl vanillidene malonate, tetrahydrocurcumenoids, tocopherol, carotenoids, anthocyanidins, hydroquinone monomethyl ether, ascorbic acid, butylated hydroxyanisole (BHA), butylated hydroxytoluene (BHT), tert-butylhydroquinone (TBHQ), propyl gallate and ethoxyquin (EMQ) and mixtures thereof. More preferably, the granulation antioxidant is alpha tocopherolacetate.

The disintegrant to be used as granulation excipient is preferably selected from the group consisting of starch, microcrystalline cellulose, alginic acid, methyl cellulose, sodium starch glycolate, croscarmellose sodium, crospovidone, calcium silicate and mixtures thereof.

The filler (or diluent) to be used as a granulation excipient is preferably selected from the group consisting of calcium carbonate, calcium phosphate (dibasic), calcium phosphate (tribasic), calcium sulphate, cellulose, microcrystalline cellulose, microcrystalline silicified cellulose, powdered cellulose, dextrates, dextrose, fructose, lactitol, lactose monohydrate (lactose), magnesium carbonate, maltitol, maltodextrin, maltose, mannitol, sodium chloride, sorbitol, starch, pregelatinized starch, sucrose, compressible sugar, sugar spheres, talc, xylitol, silicium dioxide, such as colloidal silicone dioxide (colloidal silica), silica gel, mesoporous silica or nanoporous silica; and mixtures thereof.

The binder to be used as granulation excipient is preferably selected from the group consisting of acacia mucilage, alginic acid, carbomer, carboxymethylcellulose calcium, carboxymethycellulose sodium, microcrystalline cellulose, powdered cellulose, ethyl cellulose, gelatine, liquid glucose, guar gum, hydroxyethyl cellulose, hydroxypropyl cellulose, low substituted hydroxypropyl cellulose, hydroxypropylmethyl cellulose (hypromellose), magnesium aluminum silicate, maltodextrin, methylcellulose, polydextrose, polyethylene oxide, povidone, copovidone, sodium alginate, starch paste, pregelatinized starch, sucrose (syrup), silicium dioxide and mixtures thereof. Preferably, the silicium dioxide is colloidal silicone dioxide (colloidal silica), silica gel, mesoporous silica, nanoporous silica.

The lubricant to be used as granulation excipient is preferably selected from the group consisting of calcium stearate, fumaric acid, glyceryl behenate, glyceryl palmitostearate, hydrogenated vegetable oil, magnesium lauryl sulphate, magnesium stearate, sodium lauryl sulphate, sodium stearyl fumarate, starch, stearic acid, talc, zinc stearate and mixtures thereof. In a specific embodiment is provided a process for agglomeration according to the invention wherein the granulation lubricant is selected from said group. In a specific embodiment is provided a process for granulation according to the invention wherein the granulation lubricant is selected from said group. In another specific embodiment is provided a process for preparing a tablet dosage formulation according to the invention wherein the granulation lubricant and the compression lubricant are independently selected from said group.

In preferred embodiments of the invention, the blending step comprises combining OlPC and the one or more granulation excipients in any order. In certain embodiments pre-mixes of various combinations of the respective components may be made, which pre-mixes are then combined and blended. In preferred embodiments of the invention, the blending step comprises intimate blending or mixing of the OlPC and granulation excipients to produce a homogeneous blend or mixture, employing techniques such as roller mixing, drum mixing, shear mixing, dry blending, chopping, milling, etc.

As already mentioned herein above, the process of producing the OlPC containing granulate comprises a melt-agglomeration step which results in the agglomeration/binding of primary particles of the granulation excipient and of the OlPC so as to produce granules. This step is carried out at a temperature above the melting temperature of OlPC so that OlPC is present (primarily) in a liquid state during the process. Different (wet) agglomeration techniques can be employed to accomplish this, such as extrusion granulation, high-shear granulation, low-shear granulation, or fluidized bed granulation techniques. In one particularly preferred embodiment of the invention, the melt-agglomeration step comprises hot-melt extrusion. In preferred embodiments of the invention, the temperature of the melt-agglomeration step is above the melting temperature of the OlPC and the binder. In preferred embodiments of the invention, the melt-agglomeration step, such as the hot melt extrusion step, is carried out at a temperature of at least 50° C., e.g. at a temperature of at least 60° C., at least 65° C., at least 70° C. or at least 75° C. Preferably the hot melt extrusion step, is carried out at a temperature below 120° C., e.g. at a temperature below 100° C., preferably below 90° C.

In preferred embodiments of the invention, the milling step comprises cooling said granulate, typically to below the melting temperature of the OlPC, preferably to ambient temperature. In preferred embodiments of the invention, the milling step comprises milling said cooled granulate by cutting the granulate into pieces using techniques and equipment conventionally used in the field.

Processes for Preparing Tablet Dosage Formulations

In a preferred embodiment is provided a process for preparing a tablet dosage formulation comprising a process for granulation according to the invention, a compression blending step, a compression step, and optionally a coating step,
  wherein the compression blending step comprises preparing a compression mixture by mixing an OlPC containing granulate prepared by the process according to the invention with compression excipients,
  wherein said compression excipients comprise at least a filler and a lubricant, and optionally a binder and/or a disintegrant.

This process is hereafter referred to as a process for preparing a tablet dosage formulation according to or of the invention. A tablet dosage formulation prepared via a process for granulation according to the invention, or via a process comprising such a process, as described in this embodiment, is hereafter referred to as a tablet dosage formulation according to or of the invention.

A tablet dosage formulation according to the invention may also be called a tablet dosage formulation of oleyl phosphocholine (according to the invention) in the context of this application. Hereby it is understood that a tablet dosage formulation according to the invention or a tablet dosage formulation of oleyl phosphocholine may comprise other active pharmaceutical ingredients than oleyl phosphocholine.

In an embodiment the invention provides a coating step, wherein a tablet coating is applied to the tablet dosage formulation comprising the following consecutive steps:
  sealing with a seal coating, wherein the seal coating is selected from the group consisting of shellac, zinc oxide, cellulose acetate phthalate, polyvinyl acetate phthalate, hydroxylpropylcellulose, hydroxypropylmethylcellulose or mixtures thereof;
  optionally subcoating with a subcoating comprising a sugar coating and a powder until the desired shape and consistency is achieved, wherein the sugar coating is a sucrose based solution or syrup and the powder is talc, a talc-calcium mixture, calcium carbonate or a mixture thereof;
  optionally smoothing of the tablet formulation to remove irregular features or areas of the table formulation to the required dimension;
  optionally colouring with a colour coating, wherein the colour coating is a dye or a pigment; and
  optionally polishing of the tablet formulation with a wax, wherein the wax is Montanglycolwax, beeswax or carnauba wax Fillers (or diluents) as compression excipients are preferably selected from the group consisting of calcium carbonate, calcium phosphate (dibasic), calcium phosphate (tribasic), calcium sulphate, cellulose, microcrystalline cellulose, microcrystalline silicified cellulose, powdered cellulose, dextrates, dextrose, fructose, lactitol, lactose monohydrate (lactose), magnesium carbonate, maltitol, maltodextrin, maltose, mannitol, sodium chloride, sorbitol, starch, pregelatinized starch, sucrose, compressible sugar, sugar spheres, talc, xylitol, silicium dioxide and mixtures thereof. Preferably, the silicium dioxide is colloidal silicone dioxide (colloidal silica), silica gel, mesoporous silica or nanoporous silicamore, more preferably mesoporous silica. More preferably, the compression filler in the process for preparing a tablet dosage formulation according to the invention is lactose monohydrate.

Binders as compression excipients are preferably selected from the group consisting of acacia mucilage, alginic acid, carbomer, carboxymethylcellulose calcium, carboxymethycellulose sodium, microcrystalline cellulose, powdered cellulose, ethyl cellulose, gelatine, liquid glucose, guar gum, hydroxyethyl cellulose, hydroxypropyl cellulose, low substituted hydroxypropyl cellulose, hydroxypropylmethyl cellulose (hypromellose), magnesium aluminum silicate, maltodextrin, methylcellulose, polydextrose, polyethylene oxide, povidone, copovidone, sodium alginate, starch paste, pregelatinized starch, sucrose (syrup), silicium dioxide, such as colloidal silicone dioxide, silica gel, mesoporous silica, nanoporous silicamore, more preferably mesoporous silica, and mixtures thereof. In a specific embodiment is provided a process for granulation according to the invention wherein the granulation binder is selected from said group. In another specific embodiment is provided a process for preparing a tablet dosage formulation according to the invention wherein the granulation binder and the compression binder are independently selected from said group.

More preferably, the compression binder in the process for preparing a tablet dosage formulation according to the invention is microcrystalline cellulose.

Lubricants as compression excipients are preferably selected from the group consisting of calcium stearate, fumaric acid, glyceryl behenate, glyceryl palmitostearate, hydrogenated vegetable oil, magnesium lauryl sulphate, magnesium stearate, sodium lauryl sulphate, sodium stearyl fumarate, starch, stearic acid, talc, zinc stearate and mixtures thereof.

More preferably, the compression lubricant in the process for preparing a tablet dosage formulation according to the invention is magnesium stearate.

Disintegrants as compression excipients are preferably selected from the group consisting of starch, microcrystalline cellulose, alginic acid, methyl cellulose, sodium starch glycolate, croscarmellose sodium, crospovidone, calcium silicate and mixtures thereof.

More preferably, the compression disintegrant in the process for preparing a tablet dosage formulation according to the invention is croscarmellose sodium.

Antioxidants as compression excipients are preferably selected from the group consisting of alpha tocopherolacetate, Vitamin E, Vitamin E TPGS, diethylhexyl syringylidene malonate, diisopropyl vanillidene malonate, tetrahydrocurcumenoids, tocopherol, carotenoids, anthocyanidins, hydroquinone monomethyl ether, ascorbic acid, butylated hydroxyanisole (BHA), butylated hydroxytoluene (BHT), tert-butylhydroquinone (TBHQ), propyl gallate and ethoxyquin (EMQ) and mixtures thereof.

In a preferred embodiment is provided a process for preparing a tablet dosage formulation according to the invention wherein the compression filler is lactose monohydrate; wherein the granulation binder and the compression binder are microcrystalline cellulose; wherein the granulation spacer is polyethylene glycol 6000; wherein the compression lubricant is magnesium stearate; wherein the granulation antioxidant is alpha tocopherolacetate; and wherein the granulation disintegrant and the compression disintegrant are croscarmellose sodium.

Specific Preferred Embodiments

In a preferred embodiment is provided a process for granulation according to the invention:
- wherein the concentration of oleyl phosphocholine in the OlPC containing granulate is between 10 and 50 weight percent, preferably between 25 and 35 weight percent;
- wherein, if a binder is added as a granulation excipient, the concentration of the binder in the extrudated OlPC containing granulate is between 10 and 50 weight percent, preferably between 25 and 35 weight percent, preferably wherein said binder is selected from the group consisting of acacia mucilage, alginic acid, carbomer, carboxymethylcellulose calcium, carboxymethylcellulose sodium, microcrystalline cellulose, powdered cellulose, ethyl cellulose, gelatine, liquid glucose, guar gum, hydroxyethyl cellulose, hydroxypropyl cellulose, low substituted hydroxypropyl cellulose, hydroxypropylmethyl cellulose, magnesium aluminum silicate, maltodextrin, methylcellulose, polydextrose, polyethylene oxide, povidone, copovidone, sodium alginate, starch paste, pregelatinized starch, sucrose (syrup) and mixtures thereof, most preferably wherein said binder is microcrystalline cellulose;
- wherein the concentration of the spacer in the OlPC containing granulate is between 10 and 50 weight percent, preferably between 25 and 35 weight percent, preferably wherein said spacer is selected from the group consisting of polyethylene glycol 4000, polyethylene glycol 6000, polyvinyl pyrrolidone, poly-(2-oxazoline)s and polyacrylic acid and mixtures thereof, most preferably wherein said spacer is polyethylene glycol 6000;
- wherein the concentration of the disintegrant in the OlPC containing granulate is between 1 and 20 weight percent, preferably between 1 and 10 weight percent, preferably wherein said disintegrant is selected from the group consisting of starch, microcrystalline cellulose, alginic acid, methyl cellulose, sodium starch glycolate, croscarmellose sodium, crospovidone, calcium silicate and mixtures thereof, most preferably wherein said disintegrant is croscarmellose sodium;
- wherein, if a lubricant is added as a granulation excipient, the concentration of the lubricant in the ICP containing granulate is between 1 and 20 weight percent, preferably between 1 and 10 weight percent, preferably wherein said lubricant is selected from the group consisting of calcium stearate, fumaric acid, glyceryl behenate, glyceryl palmitostearate, hydrogenated vegetable oil, magnesium lauryl sulphate, magnesium stearate, sodium lauryl sulphate, sodium stearyl fumarate, starch, stearic acid, talc, zinc stearate and mixtures thereof, most preferably wherein said lubricant is selected from the group consisting of magnesium stearate and mixtures thereof;
- wherein the concentration of the antioxidant in the OlPC containing granulate is between 0.05 and 5 weight percent, preferably between 0.1 and 1 weight percent, preferably wherein said antioxidant is selected from the group consisting of alpha tocopherolacetate, ascorbic acid, butylated hydroxyanisole (BHA), butylated hydroxytoluene (BHT), tert-butylhydroquinone (TBHQ), propyl gallate and ethoxyquin and mixtures thereof, most preferably wherein said antioxidant is alpha tocopherolacetate;
- wherein the concentrations in this embodiment are relative to the OlPC containing granulate.

In a preferred embodiment is provided a process for preparing a tablet dosage formulation according to the invention:
- wherein between 30 and 60 weight percent of OlPC containing granulate is added during the compression blending step;
- wherein the concentration of the filler in the compression mixture is between 10 and 40 weight percent, preferably between 25 and 35 weight percent, preferably wherein said filler is selected from the group consisting of calcium carbonate, calcium phosphate (dibasic), calcium phosphate (tribasic), calcium sulphate, cellulose, microcrystalline cellulose, microcrystalline silicified cellulose, powdered cellulose, dextrates, dextrose, fructose, lactitol, lactose monohydrate, magnesium carbonate, maltitol, maltodextrin, maltose, mannitol, sodium chloride, sorbitol, starch, pregelatinized starch, sucrose, compressible sugar, sugar spheres, talc, xylitol and mixtures thereof, most preferably wherein said filler is lactose monohydrate;
- wherein the concentration of the lubricant in the compression mixture is between 10 and 30 weight percent, preferably between 15 and 25 weight percent, preferably wherein said lubricant is selected from the group consisting of calcium stearate, fumaric acid, glyceryl behenate, glyceryl palmitostearate, hydrogenated vegetable oil, magnesium lauryl sulphate, magnesium stearate, sodium lauryl sulphate, sodium stearyl fumarate, starch, stearic acid, talc, zinc stearate and mixtures thereof, most preferably wherein said lubricant is selected from the group consisting of magnesium stearate, and mixtures thereof;
- wherein the concentrations in this embodiment are relative to the compression mixture.

In an embodiment of the invention is provided a process for preparing a tablet dosage formulation as defined herein:
- wherein the concentration of oleyl phosphocholine in the tablet dosage formulation is between 5 and 40 weight percent, preferably between 15 and 30 weight percent;
- wherein the concentration of the filler in the tablet dosage formulation is between 20 and 70 weight percent, preferably between 30 and 60 weight percent, preferably wherein said filler is selected from the group consisting of calcium carbonate, calcium phosphate (dibasic), calcium phosphate (tribasic), calcium sulphate, cellulose, microcrystalline cellulose, microcrystalline silicified cellulose, powdered cellulose, dextrates, dextrose, fructose, lactitol, lactose, lactose monohydrate, magnesium carbonate, maltitol, maltodextrin, maltose, mannitol, sodium chloride, sorbitol, starch, pregelatinized starch, sucrose, compressible sugar, sugar spheres, talc, xylitol, silicium dioxide, such as colloidal silicone dioxide, silica gel, mesoporous silica or nanoporous silica, and mixtures thereof, most preferably wherein said filler is lactose and colloidal silicone dioxide;

wherein the concentration of the binder in the tablet dosage formulation is between 10 and 40 weight percent, preferably between 15 and 30 weight percent, preferably wherein said binder is selected from the group consisting of acacia mucilage, alginic acid, carbomer, carboxymethylcellulose calcium, carboxymethycellulose sodium, microcrystalline cellulose, powdered cellulose, ethyl cellulose, gelatine, liquid glucose, guar gum, hydroxyethyl cellulose, hydroxypropyl cellulose, low substituted hydroxypropyl cellulose, hydroxypropylmethyl cellulose, magnesium aluminum silicate, maltodextrin, methylcellulose, polydextrose, polyethylene oxide, povidone, copovidone, sodium alginate, starch paste, pregelatinized starch, sucrose (syrup) and mixtures thereof, most preferably wherein said binder is microcrystalline cellulose and hydroxypropylmethyl cellulose;

wherein the concentration of the disintegrant in the tablet dosage formulation is between 1 and 5 weight percent, preferably between 2 and 4 weight percent, preferably wherein said disintegrant is selected from the group consisting of starch, microcrystalline cellulose, alginic acid, methyl cellulose, sodium starch glycolate, croscarmellose sodium, crospovidone, calcium silicate and mixtures thereof, most preferably wherein said disintegrant is croscarmellose sodium;

wherein the concentration of the lubricant in the tablet dosage formulation is between 0.1 and 2 weight percent, preferably between 0.5 and 1 weight percent, preferably wherein said lubricant is selected from the group consisting of calcium stearate, fumaric acid, glyceryl behenate, glyceryl palmitostearate, hydrogenated vegetable oil, magnesium lauryl sulphate, magnesium stearate, sodium lauryl sulphate, sodium stearyl fumarate, starch, stearic acid, talc, zinc stearate and mixtures thereof, most preferably wherein said lubricant is magnesium stearate;

wherein the concentration of the antioxidant in the tablet dosage formulation is between 0.1 and 2 weight percent, preferably between 0.5 and 1 weight percent, preferably wherein said antioxidant is selected from the group consisting of alpha tocopherolacetate, ascorbic acid, butylated hydroxyanisole (BHA), butylated hydroxytoluene (BHT), tert-butylhydroquinone (TBHQ), propyl gallate and ethoxyquin and mixtures thereof, most preferably wherein said antioxidant is vitamin E;

wherein the concentrations in this embodiment are relative to the tablet dosage formulation.

In a preferred embodiment a process for preparing a tablet dosage formulation according to the invention is provided, wherein the tablet dosage formulation comprises oleyl phosphocholine, lactose, colloidal silica, microcrystalline cellulose, hydroxypropylmethyl cellulose, croscarmellose sodium, magnesium stearate and vitamin E:

wherein the concentration of oleyl phosphocholine in the tablet dosage formulation is between 5 and 40 weight percent, preferably between 15 and 30 weight percent;

wherein the concentration of the lactose in the tablet dosage formulation is between 5 and 25%, preferably between 10 and 20%;

wherein the concentration of the colloidal silica in the table dosage formulation is between 15 and 45%, preferably between 20 and 40%;

wherein the concentration of the microcrystalline cellulose in the tablet dosage formulation is between 5 and 25 weight percent, preferably between 10 and 20 weight percent;

wherein the concentration of the hydroxypropylmethyl cellulose in the tablet dosage formulation is between 5 and 15 weight percent, preferably between 5 and 10 weight percent;

wherein the concentration of the croscarmellose sodium in the tablet dosage formulation is between 1 and 5 weight percent, preferably between 2 and 4 weight percent;

wherein the concentration of the magnesium stearate in the tablet dosage formulation is between 0.1 and 2 weight percent, preferably between 0.5 and 1 weight percent;

wherein the concentration of the vitamin E in the tablet dosage formulation is between 0.1 and 2 weight percent, preferably between 0.5 and 1 weight percent;

wherein the concentrations in this embodiment are relative to the tablet dosage formulation.

Tablet Dosage Formulations

The present invention provides a tablet dosage formulation prepared via a process for granulation according to the invention, or via a process comprising such a process, such as a process for preparing a tablet dosage formulation according to the invention. As explained above, said tablet dosage formulation is called a tablet dosage formulation according to the invention, and may comprise further active pharmaceutical ingredients besides oleyl phosphocholine.

In a preferred embodiment is provided a tablet dosage formulation according to the invention:

wherein the concentration of oleyl phosphocholine in the tablet dosage formulation is between 5 and 20 weight percent, preferably between 5 and 15 weight percent;

wherein the concentration of the filler in the tablet dosage formulation is between 10 and 30 weight percent, preferably between 15 and 25 weight percent, preferably wherein said filler is selected from the group consisting of calcium carbonate, calcium phosphate (dibasic), calcium phosphate (tribasic), calcium sulphate, cellulose, microcrystalline cellulose, microcrystalline silicified cellulose, powdered cellulose, dextrates, dextrose, fructose, lactitol, lactose monohydrate, magnesium carbonate, maltitol, maltodextrin, maltose, mannitol, sodium chloride, sorbitol, starch, pregelatinized starch, sucrose, compressible sugar, sugar spheres, talc, xylitol and mixtures thereof, most preferably wherein said filler is lactose monohydrate;

wherein, if a binder is added during the process for preparing said tablet dosage formulation, the concentration of the binder in the tablet dosage formulation is between 10 and 30 weight percent, preferably between 15 and 25 weight percent, preferably wherein said binder is selected from the group consisting of acacia mucilage, alginic acid, carbomer, carboxymethylcellulose calcium, carboxymethycellulose sodium, microcrystalline cellulose, powdered cellulose, ethyl cellulose, gelatine, liquid glucose, guar gum, hydroxyethyl cellulose, hydroxypropyl cellulose, low substituted hydroxypropyl cellulose, hydroxypropylmethyl cellulose, magnesium aluminum silicate, maltodextrin, methylcellulose, polydextrose, polyethylene oxide, povidone, copovidone, sodium alginate, starch paste, pregelatinized starch, sucrose (syrup) and mixtures thereof, most preferably wherein said binder is microcrystalline cellulose;

wherein the concentration of the spacer in the tablet dosage formulation is between 10 and 30 weight percent, preferably between 15 and 25 weight percent, preferably wherein said spacer is selected from the group consisting of polyethylene glycol 4000, polyethylene glycol 6000, polyvinyl pyrrolidone, poly-(2-oxazoline)s and polyacrylic acid and mixtures thereof, most preferably wherein said spacer is polyethylene glycol 6000;

wherein the concentration of the disintegrant in the tablet dosage formulation is between 1 and 10 weight percent, preferably between 1 and 5 weight percent, preferably wherein said disintegrant is selected from the group consisting of starch, microcrystalline cellulose, alginic acid, methyl cellulose, sodium starch glycolate, croscarmellose sodium, crospovidone, calcium silicate and mixtures thereof, most preferably wherein said disintegrant is croscarmellose sodium;

wherein the concentration of the lubricant in the tablet dosage formulation is between 5 and 20 weight percent, preferably between 5 and 15 weight percent, preferably wherein said lubricant is selected from the group consisting of calcium stearate, fumaric acid, glyceryl behenate, glyceryl palmitostearate, hydrogenated vegetable oil, magnesium lauryl sulphate, magnesium stearate, sodium lauryl sulphate, sodium stearyl fumarate, starch, stearic acid, talc, zinc stearate and mixtures thereof, most preferably wherein said lubricant is selected from the group consisting of magnesium stearate, and mixtures thereof;

wherein the concentration of the antioxidant in the tablet dosage formulation is between 0.05 and 5 weight percent, preferably between 0.1 and 1 weight percent, preferably wherein said antioxidant is selected from the group consisting of alpha tocopherolacetate, ascorbic acid, butylated hydroxyanisole (BHA), butylated hydroxytoluene (BHT), tert-butylhydroquinone (TBHQ), propyl gallate and ethoxyquin and mixtures thereof, most preferably wherein said antioxidant is alpha tocopherolacetate;

wherein the concentrations in this embodiment are relative to the tablet dosage formulation.

In a preferred embodiment a tablet dosage formulation according to the invention is provided:

wherein the concentration of oleyl phosphocholine in the tablet dosage formulation is between 5 and 40 weight percent, preferably between 15 and 30 weight percent;

wherein the concentration of the filler in the tablet dosage formulation is between 20 and 70 weight percent, preferably between 30 and 60 weight percent, preferably wherein said filler is selected from the group consisting of calcium carbonate, calcium phosphate (dibasic), calcium phosphate (tribasic), calcium sulphate, cellulose, microcrystalline cellulose, microcrystalline silicified cellulose, powdered cellulose, dextrates, dextrose, fructose, lactitol, lactose, lactose monohydrate, magnesium carbonate, maltitol, maltodextrin, maltose, mannitol, sodium chloride, sorbitol, starch, pregelatinized starch, sucrose, compressible sugar, sugar spheres, talc, xylitol, silicium dioxide, such as colloidal silicone dioxide, silica gel, mesoporous silica or nanoporous silica, and mixtures thereof, most preferably wherein said filler is lactose and colloidal silicone dioxide;

wherein, the concentration of the binder in the tablet dosage formulation is between 10 and 40 weight percent, preferably between 15 and 30 weight percent, preferably wherein said binder is selected from the group consisting of acacia mucilage, alginic acid, carbomer, carboxymethylcellulose calcium, carboxymethycellulose sodium, microcrystalline cellulose, powdered cellulose, ethyl cellulose, gelatine, liquid glucose, guar gum, hydroxyethyl cellulose, hydroxypropyl cellulose, low substituted hydroxypropyl cellulose, hydroxypropylmethyl cellulose, magnesium aluminum silicate, maltodextrin, methylcellulose, polydextrose, polyethylene oxide, povidone, copovidone, sodium alginate, starch paste, pregelatinized starch, sucrose (syrup) and mixtures thereof, most preferably wherein said binder is microcrystalline cellulose and hydroxypropylmethyl cellulose;

wherein the concentration of the disintegrant in the tablet dosage formulation is between 1 and 5 weight percent, preferably between 2 and 4 weight percent, preferably wherein said disintegrant is selected from the group consisting of starch, microcrystalline cellulose, alginic acid, methyl cellulose, sodium starch glycolate, croscarmellose sodium, crospovidone, calcium silicate and mixtures thereof, most preferably wherein said disintegrant is croscarmellose sodium;

wherein the concentration of the lubricant in the tablet dosage formulation is between 0.1 and 2 weight percent, preferably between 0.5 and 1 weight percent, preferably wherein said lubricant is selected from the group consisting of calcium stearate, fumaric acid, glyceryl behenate, glyceryl palmitostearate, hydrogenated vegetable oil, magnesium lauryl sulphate, magnesium stearate, sodium lauryl sulphate, sodium stearyl fumarate, starch, stearic acid, talc, zinc stearate and mixtures thereof, most preferably wherein said lubricant is magnesium stearate;

wherein the concentration of the antioxidant in the tablet dosage formulation is between 0.1 and 2 weight percent, preferably between 0.5 and 1 weight percent, preferably wherein said antioxidant is selected from the group consisting of alpha tocopherolacetate, ascorbic acid, butylated hydroxyanisole (BHA), butylated hydroxytoluene (BHT), tert-butylhydroquinone (TBHQ), propyl gallate and ethoxyquin and mixtures thereof, most preferably wherein said antioxidant is vitamin E;

wherein the concentrations in this embodiment are relative to the tablet dosage formulation.

In an embodiment a tablet dosage formulation according to the invention is provided, wherein the tablet dosage formulation comprises oleyl phosphocholine, lactose, colloidal silica, microcrystalline cellulose, hydroxypropylmethyl cellulose, croscarmellose sodium, magnesium stearate and vitamin E:

wherein the concentration of oleyl phosphocholine in the tablet dosage formulation is between 5 and 40 weight percent, preferably between 15 and 30 weight percent;

wherein the concentration of the lactose in the tablet dosage formulation is between 5 and 25%, preferably between 10 and 20%;

wherein the concentration of the colloidal silica in the table dosage formulation is between 15 and 45%, preferably between 20 and 40%;

wherein the concentration of the microcrystalline cellulose in the tablet dosage formulation is between 5 and 25 weight percent, preferably between 10 and 20 weight percent;

wherein the concentration of the hydroxypropylmethyl cellulose in the tablet dosage formulation is between 5 and 15 weight percent, preferably between 5 and 10 weight percent;

wherein the concentration of the croscarmellose sodium in the tablet dosage formulation is between 1 and 5 weight percent, preferably between 2 and 4 weight percent;

wherein the concentration of the magnesium stearate in the tablet dosage formulation is between 0.1 and 2 weight percent, preferably between 0.5 and 1 weight percent;

wherein the concentration of the vitamin E in the tablet dosage formulation is between 0.1 and 2 weight percent, preferably between 0.5 and 1 weight percent;

wherein the concentrations in this embodiment are relative to the tablet dosage formulation.

In an embodiment, the invention provides the tablet dosage formulation as defined herein further comprising a tablet coating, wherein the tablet coating comprises a seal coating, a subcoating, and a colour coating;

wherein the seal coating is selected from the group consisting of shellac, zinc oxide, cellulose acetate phthalate, polyvinyl acetate phthalate, hydroxylpropylcellulose, hydroxypropylmethylcellulose and mixtures thereof and wherein the concentration of the seal coating is between 1 and 3 weight percent;

wherein the subcoating comprises a sugar coating and a powder, wherein the sugar coating is a sucrose based solution or syrup, wherein the powder is talc, talc-calcium mixture, calcium carbonate or mixtures thereof and wherein the concentration of the subcoating is between 70 and 80 weight percent;

wherein the colour coating is a dye or a pigment and wherein the concentration of the colour coating is between 20 and 30 weight percent;

wherein the wax is Montanglycolwax, beeswax or carnauba wax and wherein the concentration of the wax is less than 0.01 weight percent;

wherein the concentrations in this embodiment are relative to the tablet coating.

The preparation and composition of tablet dosage formulations according to the invention is shown in Examples 1 and 2.

The present invention provides tablet dosage formulations of oleyl phosphocholine which are particularly stable. Specifically, in one embodiment of the present invention is provided a tablet dosage formulation according to the invention wherein, if stored under warm and humid conditions,
the concentration of each active pharmaceutical ingredient in said tablet dosage formulation does not change by more than 5 weight percent, preferably by not more than 2.5 weight percent, more preferably by not more than 1 weight percent; and/or
each active pharmaceutical ingredient in said tablet dosage formulation has a stable dissolution release profile;
wherein storage, in the order of increasing preference, is for 1, 2, 3, 6, 12, 18, 24 or 36 months;
wherein warm conditions correspond to a temperature range from 20° C. to 60° C., wherein more preferred temperature ranges are, in the order of increasing preference, from 25° C. to 60° C., from 30° C. to 60° C., from 35° C. to 60° C., and from 40° C. to 60° C.,
wherein humid conditions correspond to a relative humidity range from 20% to 100%, wherein more preferred relative humidity ranges are, in the order of increasing preference, are from 50% to 100%, from 60% to 100%, from 65% to 100%, from 70% to 100%, and from 75% to 100%,
preferably wherein warm and humid conditions correspond to 25° C. and 60% RH or 30° C. and 65% RH or 30° C. and 75% RH or 40° C. and 75% RH for 12 or 24 months; more preferably 25° C. and 60% RH or 30° C. and 65% RH or 30° C. and 75% RH or 40° C. and 75% RH for 24 months; more preferably 30° C. and 75% RH or 40° C. and 75% RH for 24 months; most preferably 30° C. and 75% RH for 24 months.

The stability of tablet dosage formulations according to the invention, and the stable dissolution release profile of oleyl phosphocholine comprised in said tablets, is demonstrated in Examples 3 and 4, respectively.

As discussed above, a tablet dosage formulation according to the invention is more stable under warm and humid conditions than a tablet dosage formulations prepared via a direct compression or a wet granulation process and not comprising a spacer and an antioxidant, as found in the prior art.

Medical uses of Tablet Dosage Formulations

A tablet dosage formulation according to the invention is provided for use as a medicament. In a preferred embodiment is provided a tablet dosage formulation according to the invention for use in the treatment of parasitic diseases, preferably a parasitic disease selected from the group consisting of leishmaniasis, chagas or malaria and cancer.

EXAMPLES

The following examples are offered for illustrative purposes only, and are not intended to limit the scope of the present invention in any way.

Example 1: Milled Extrudate

In this example is provided a milled extrudate, as described in this application. The composition of this milled extrudate is given in Table 1.

TABLE 1

Composition of milled extrudate

| | | mass (mg per tablet) | % in the milled extrudate (157.730 mg milled extrudate per tablet) |
|---|---|---|---|
| API | oleyl phosphocholine | 50.000 | 31.700 |
| Granulation excipient | alpha tocopherol-acetate | 1.000 | 0.634 |
| | microcrystalline cellulose | 49.000 | 31.066 |
| | macrogol 6000 | 50.000 | 31.700 |
| | sodium croscarmellose | 7.730 | 4.901 |
| Sum | | 157.730 | 100.000 |

Example 2: Tablet Dosage Formulation

In this example is provided a tablet dosage formulation prepared via a process for preparing a tablet dosage formulation according to the invention. In this process, the milled extrudate as described in Example 1 was an intermediate.

The composition of the compression mixture in this example, prepared as an intermediate during the process for preparing a tablet dosage formulation according to the invention, is given in Table 2.

The composition of the tablet dosage formulation in this example is given in Table 3. The composition of the tablet coating of the tablet dosage formulation in this example is given in Table 4.

Figure 1:
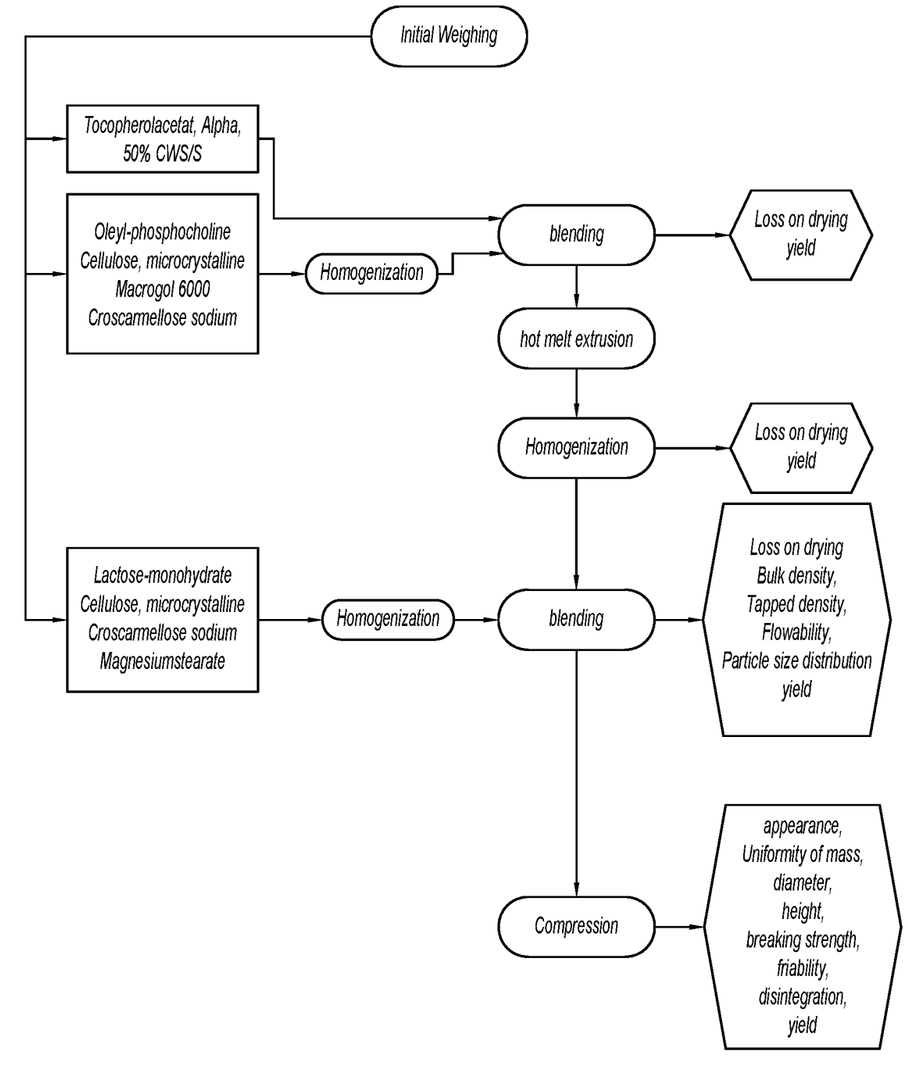
FIG. 1: Process for preparing the tablet core of the tablet dosage formulation in Example 1.

The tablet core of the tablet dosage formulation in this example was prepared via the process steps as described in FIG. 1.

TABLE 2

Composition of the compression mixture

|  |  | mass (mg per tablet) |
|---|---|---|
| Compression excipient | lactose monohydrate | 97.920 |
|  | microcrystalline cellulose | 47.250 |
|  | sodium croscarmellose | 9.350 |
|  | magnesium stearate | 3.150 |
| Sum |  | 157.670 |
| Milled extrudate |  | 157.730 |
| Compression mixture |  | 315.400 |

TABLE 3

Composition of tablet dosage formulation

|  |  | mass (mg per tablet) | % in the tablet dosage formulation (557.700 mg per tablet) |
|---|---|---|---|
| API | oleyl phosphocholine | 50.000 | 8.965 |
| Excipient | alpha tocopherol-acetate | 1.000 | 0.180 |
|  | microcrystalline cellulose | 96.250 | 17.258 |
|  | macrogol 6000 | 50.000 | 8.965 |
|  | sodium croscarmellose | 17.080 | 3.062 |
|  | lactose monohydrate | 97.920 | 17.558 |
|  | magnesium stearate | 3.150 | 0.565 |
| Coating |  | 242.300 | 43.446 |
| Sum |  | 557.700 | 100.00 |

TABLE 4

Composition of the tablet coating

|  | mass (mg per tablet) |
|---|---|
| Seal coating | 3.976 |
| Talc | 0.904 |
| Sugar coating | 19.605 |
| Talc-calcium mixture | 31.679 |
| Sugar coating | 129.870 |

TABLE 4-continued

Composition of the tablet coating

|  | mass (mg per tablet) |
|---|---|
| Colour coating | 56.112 |
| Motanylglycolwax | 0.160 |
| Sum | 234.600 |

Example 3: Stability of a Tablet Dosage Formulation

The change of the concentration of oleyl phosphocholine in the tablet dosage formulation described in Example 2 upon storage under different conditions can be found in Table 5.

TABLE 5

Change of oleyl phosphocholine concentration

| Conditions |  | OlPC concentration in the tablet dosage formulation (mg/tablet) after X months of storage |  |  |  |  |  |
|---|---|---|---|---|---|---|---|
| T | RH | X = 0 | X = 3 | X = 6 | X = 18 | X = 24 | X = 36 |
| 25° C. | 60% | 50.2 | 48.1 | 48.1 | 49.15 | 47.10 | 50.14 |
| 30° C. | 75% | 50.2 | 47.5 | 49.7 | 50.17 | 47.46 | 49.30 |
| 40° C. | 75% | 50.2 | 48.9 | 49.9 |  |  |  |

Example 4: Dissolution of Oleyl Phosphocholine

The dissolution of oleyl phosphocholine comprised in the tablet dosage formulation described in Example 2, which has been stored for different time periods (18 months, 24 months, 36 months) under different conditions, has been determined by the European Pharmacopoeia 2.9.3 standard dissolution test after 60 minutes. The results can be found in Table 6.

TABLE 6

Dissolution of oleyl phosphocholine concentration

| Conditions |  | Dissolved weight percentage of oleyl phosphocholine after 60 minutes, relative to the tablet dosage formulation |  |  |
|---|---|---|---|---|
|  |  | storage of | storage of | storage of |
| T | RH | 18 months | 24 months | 36 months |
| 25° C. | 60% | 78.4 | 83.2 | 96.4 |
| 30° C. | 75% | 89.9 | 80.9 | 83.3 |

The invention claimed is:

1. A process for making an olelyl phosphocholine (OlPC) containing granulate, said process comprising a blending step, a hot melt extrusion step and a milling step,
   wherein the blending step comprises preparing a granulation mixture of olelyl phosphocholine and granulation excipients, wherein said granulation excipients comprise at least a spacer, an antioxidant and a disintegrant, and optionally a binder and/or a lubricant;
   wherein the hot melt extrusion step comprises preparing an extrudate by heating said granulation mixture at a temperature of at least 50° C. and below 90° C. and extrudating said heated granulation mixture;

wherein the milling step comprises cooling said extrudate and milling said cooled extrudate to obtain a milled extrudate;

wherein no solvent is added during the process for granulation, wherein the concentration of oleyl phosphocholine in the milled extrudate is between 10 and 50 weight percent, wherein, if a binder is added as a granulation excipient, the concentration of the binder in the milled extrudate is between 10 and 50 weight percent, wherein, if a lubricant is added as a granulation excipient, the concentration of the lubricant in the milled extrudate is between 1 and 20 weight percent, wherein the concentration of the antioxidant in the milled extrudate is between 0.05 and 5 weight percent, wherein the concentration of the disintegrant in the milled extrudate is between 1 and 20 weight percent, wherein the concentration of the spacer in the milled extrudate is between 10 and 50 weight percent, and wherein the concentrations are relative to the milled extrudate.

2. The process according to claim 1, wherein the mixture comprises a spacer selected from the group consisting of polyethylene glycol, polyethylene glycol esters, polypropylene glycol, polypropylene glycol esters, polyvinyl pyrrolidone (PVP), poly-(2-oxazoline)s (POX), polyacrylic acid (PAA), hydroxypropylmethylcellulose and mixtures thereof.

3. The process according to claim 1, wherein the mixture comprises an antioxidant selected from the group consisting of alpha tocopherolacetate, Vitamin E, Vitamin E TPGS, diethylhexyl syringylidene malonate, diisopropyl vanillidene malonate, tetrahydrocurcumenoids, tocopherol, carotenoids, anthocyanidins, hydroquinone monomethyl ether, ascorbic acid, butylated hydroxyanisole (BHA), butylated hydroxytoluene (BHT), tert-butylhydroquinone (TBHQ), propyl gallate and ethoxyquin (EMQ) and mixtures thereof.

4. The process according to claim 1, wherein the mixture comprises a filler selected from the group consisting of calcium carbonate, calcium phosphate (dibasic), calcium phosphate (tribasic), calcium sulphate, cellulose, microcrystalline cellulose, microcrystalline silicified cellulose, powdered cellulose, dextrates, dextrose, fructose, lactitol, lactose monohydrate, magnesium carbonate, maltitol, maltodextrin, maltose, mannitol, sodium chloride, sorbitol, starch, pregelatinized starch, sucrose, compressible sugar, sugar spheres, talc, xylitol, silicium dioxide, and mixtures thereof.

5. A process for preparing a tablet dosage formulation comprising a process for making an OlPC containing granulate according to claim 1, a blending step, a compression step, and optionally a coating step, wherein the blending step comprises preparing a compression mixture by mixing the OlPC containing granulate with compression excipients, wherein said compression excipients comprise at least a filler and a lubricant, and optionally a binder and/or a disintegrant.

6. The process for preparing a tablet dosage formulation according to claim 5, wherein between 30 and 60 weight percent of the OlPC containing granulate is added during the blending step;

wherein the concentration of the filler in the compression mixture is between 10 and 40 weight percent, preferably between 25 and 35 weight percent;

wherein the concentration of the lubricant in the compression mixture is between 10 and 30 weight percent, preferably between 15 and 25 weight percent;

wherein the concentrations are relative to the compression mixture.

7. The process for preparing a tablet dosage formulation according to claim 5, wherein the tablet dosage formulation comprises oleyl phosphocholine, lactose, colloidal silica, microcrystalline cellulose, hydroxypropylmethyl cellulose, croscarmellose sodium, magnesium stearate and vitamin E:

wherein the concentration of oleyl phosphocholine in the tablet dosage formulation is between 5 and 40 weight percent;

wherein the concentration of the lactose in the tablet dosage formulation is between 5 and 25%, wherein the concentration of the colloidal silica in the table dosage formulation is between 15 and 45%, wherein the concentration of the microcrystalline cellulose in the tablet dosage formulation is between 5 and 25 weight percent, wherein the concentration of the hydroxypropylmethyl cellulose in the tablet dosage formulation is between 5 and 15 weight percent, wherein the concentration of the croscarmellose sodium in the tablet dosage formulation is between 1 and 5 weight percent, wherein the concentration of the magnesium stearate in the tablet dosage formulation is between 0.1 and 2 weight percent, wherein the concentration of the vitamin E in the tablet dosage formulation is between 0.1 and 2 weight percent, and wherein the concentrations are relative to the compression mixture.

8. A tablet dosage formulation obtainable by the process according to claim 5.

9. The tablet dosage formulation according to claim 8, wherein the concentration of oleyl phosphocholine in the tablet dosage formulation is between 5 and 20 weight percent;

wherein the concentration of the filler in the tablet dosage formulation is between 10 and 30 weight percent;

wherein the concentration of the binder in the tablet dosage formulation is between 10 and 30 weight percent;

wherein the concentration of the disintegrant in the tablet dosage formulation is between 1 and 10 weight percent;

wherein the concentration of the lubricant in the tablet dosage formulation is between 5 and 20 weight percent;

wherein the concentration of the antioxidant in the tablet dosage formulation is between 0.05 and 5 weight percent;

wherein the concentration of the spacer in the tablet dosage formulation is between 5 and 20 weight percent; and wherein the concentrations are relative to the tablet dosage formulation.

10. The tablet dosage formulation according to claim 8, wherein the tablet dosage formulation comprises oleyl phosphocholine, lactose, colloidal silica, microcrystalline cellulose, hydroxypropylmethyl cellulose, croscarmellose sodium, magnesium stearate and vitamin E:

wherein the concentration of oleyl phosphocholine in the tablet dosage formulation is between 5 and 40 weight percent;

wherein the concentration of the lactose in the tablet dosage formulation is between 5 and 25%;
wherein the concentration of the colloidal silica in the table dosage formulation is between 15 and 45%;
wherein the concentration of the microcrystalline cellulose in the tablet dosage formulation is between 5 and 25 weight percent;
wherein the concentration of the hydroxypropylmethyl cellulose in the tablet dosage formulation is between 5 and 15 weight percent;
wherein the concentration of the croscarmellose sodium in the tablet dosage formulation is between 1 and 5 weight percent;
wherein the concentration of the magnesium stearate in the tablet dosage formulation is between 0.1 and 2 weight percent;
wherein the concentration of the vitamin E in the tablet dosage formulation is between 0.1 and 2 weight percent; and
wherein the concentrations are relative to the compression mixture.

11. The tablet dosage formulation according to claim 8 comprising a tablet coating, wherein the tablet coating comprises a seal coating, a subcoating, and a colour coating;
wherein the seal coating is selected from the group consisting of shellac, zinc oxide, cellulose acetate phthalate, polyvinyl acetate phthalate, hydroxylpropylcellulose, hydroxypropylmethylcellulose and mixtures thereof and wherein the concentration of the seal coating is between 1 and 3 weight percent;
wherein the subcoating comprises a sugar coating and a powder, wherein the sugar coating is a sucrose based solution or syrup, wherein the powder is talc, talc-calcium mixture, calcium carbonate or mixtures thereof and wherein the concentration of the subcoating is between 70 and 80 weight percent;
wherein the colour coating is a dye or a pigment and wherein the concentration of the colour coating is between 20 and 30 weight percent;
wherein the wax is Montanglycolwax, beeswax or carnauba wax and wherein the concentration of the wax is less than 0.01 weight percent;
wherein the concentrations in this embodiment are relative to the tablet coating.

12. The tablet dosage formulation according to claim 8, wherein, if said tablet dosage formulation is stored for at least 24 months at a temperature of 30° C. and at a relative humidity of 75%,
the concentration of each active pharmaceutical ingredient in said tablet dosage formulation does not change by more than 2.5 weight percent, preferably by no more than 1 weight percent; and
each active pharmaceutical ingredient in said tablet dosage formulation has a stable dissolution release profile.

13. A method for treating a parasitic disease, the method comprising administering the tablet dosage formulation according to claim 8 to a subject in need thereof.

14. The method of claim 13, wherein the method is for the treatment of a parasitic disease selected from the group consisting of leishmaniasis, chagas, malaria and cancer.

* * * * *